United States Patent [19]

Saito et al.

[11] Patent Number: 4,956,392
[45] Date of Patent: Sep. 11, 1990

[54] PROCESS FOR PRODUCING METHANOL OR MIXED ALCOHOL

[75] Inventors: Yoshihiko Saito; Osamu Hashimoto; Masaaki Kuwa; Takashi Kojima; Kinya Tsuji, all of Niigata, Japan

[73] Assignee: Mitsubishi Gas Chemical Company, Inc., Tokyo, Japan

[21] Appl. No.: 437,314

[22] Filed: Nov. 17, 1989

Related U.S. Application Data

[63] Continuation of Ser. No. 160,280, Feb. 25, 1988, abandoned.

[30] Foreign Application Priority Data

Feb. 27, 1987 [JP] Japan ................................. 62-43021

[51] Int. Cl.$^5$ ..................... C07C 27/06; C07C 27/08
[52] U.S. Cl. .................................... 518/712; 518/713
[58] Field of Search ................................ 518/712, 713

[56] References Cited

U.S. PATENT DOCUMENTS 2,573,795 11/1951 Lanning .
2,620,262 12/1952 Hujsak et al. .
4,666,945 5/1987 Osugi et al. .

FOREIGN PATENT DOCUMENTS 84142 6/1985 Japan .
122040 6/1985 Japan .
2076423 12/1981 United Kingdom .

OTHER PUBLICATIONS

Translation for Japan 60-84142.

Primary Examiner—Howard T. Mars
Attorney, Agent, or Firm—Wenderoth, Lind & Ponack

[57] ABSTRACT

A process for producing methanol or mixed alcohol which comprises reacting a synthesis gas containing hydrogen and carbon monoxide and/or carbon dioxide in a fluidized catalyst bed.

Catalyst particles having an average particle diameter of not more than 150 microns and a particle density of at least 1.7 g/cm$^3$ are used as the fluidized catalyst.

The catalyst particles are contacted with the synthesis gas at a superficial linear velocity of at least 0.2 m/sec. under a pressure of 40 to 200 atmospheres.

6 Claims, 1 Drawing Sheet

PROCESS FOR PRODUCING METHANOL OR MIXED ALCOHOL

This application is a continuation of now abandoned application Ser. No. 160,280, filed on Feb. 25, 1988.

This invention relates to an improved process for producing methanol or mixed alcohol from synthesis gas, and more specifically to a process for highly efficiently producing methanol or mixed alcohol mainly used as a fuel from synthesis gas in goods yields using a fluidized bed catalyst.

The production of methanol from synthesis gas as a starting material using a fluidized bed catalyst has recently aroused interest because it permits simplification of the structure of the reactor used and the utilization of the heat of reaction is easy [see a Japanese-language publication, "Chemical Engineering", 25, (8), pages 9–15 (1980)].

Catalysts for use in the production of methanol by this fluidized bed catalyst process have also been developed. For example, Japanese Laid-Open Patent Publications Nos. 84142/1985 and 122040/1985 disclosed processes for producing fluidized bed catalyst of the copper-zinc-aluminum type, and U.S. Pat. No. 4,666,945 discloses a process for producing a fluidized bed catalyst of the copper-zinc-zirconium type.

Methanol has been widely used as a basic material in the chemical industry, and recently attracted attention for use as an energy-producing source, such as a substitute fuel for power generating boilers and an automobile fuel. Large apparatus for production of methanol have been constructed which have a daily production capacity of several thousand tons.

There have also been developed apparatus for production of mixed alcohol composed of methanol and higher alcohols such as ethanol, propanol and butanol which is mainly used as a fuel.

In the prior art, methanol from synthesis gas is produced mainly in a reactor having a fixed bed catalyst, and various contrivances are made for temperature control of the catalyst layer and the recovery of the heat of reaction. However, development of a large-sized apparatus using a reactor with a fixed bed catalyst has the following problems.

(1) For temperature control of the catalyst bed, a quenching method is generally employed by which an unreacted cooling gas is injected among catalyst layers. To remove a large quantity of heat of the reaction and maintain the catalyst bed at a proper reaction temperature, it is necessary to divide the catalyst bed into a multiplicity of catalyst layers and inject a large quantity of a quenching gas into the catalyst bed. It is difficult in practice therefore to maintain the concentration of methanol at the exit of the reactor at more than 5% in the quenching-type reactor. Moreover, the production rate per unit amount of catalyst (to be referred to as "STY" hereinafter) cannot be maintained high. Accordingly, with an increase in the size of the apparatus, the diameter of the reactor and the size of piping connected to the reactor have remarkably increased. Consequently, the production capacity in one train is generally limited to 3,000 tons/day at most.

Since the quenching method requires circulation of a large amount of gas and the pressure drop in the catalyst layers increases, the required power markedly increases.

Furthermore, since in the quenching method, most of the heat of the reaction is used for heating the quenching gas, only a small quantity of the heat of reaction is recovered from the outlet gas of the reactor. No efficient recovery of the heat of the reaction can therefore be effected.

For the foregoing reasons, the quenching method has only limited effect for reducing the quantity of energy required for production of a unit amount of methanol (to be referred to as the "energy unit").

(2) A method has also been employed in which a vertical multitubular heat exchanger is used as the reactor and the catalyst is filled in the tubes. This method is better than the quenching method insofar as a large quantity of the heat of the reaction can be efficiently recovered. However, according to this method, the reaction at the inlet portion of the catalyst layer takes place vigorously and an abrupt temperature increase occurs at this portion. To prevent it, it is necessary to limit the concentration of the effective components, i.e. carbon oxides ($CO+CO_2$), of the gas fed to the reactor to a lower value, or increase the amount of the circulating gas as in the quenching method reactor. Consequently, the concentration of methanol at the outlet of the reactor is at most 6 to 8%.

For the foregoing reason, the catalyst is not used sufficiently uniformly and effectively in this method. Although STY can be higher in this method than in the quenching method, it is still not sufficient.

Furthermore, in the reactor used in this method, many slender reaction tubes must be provided in order to remove a large quantity of the heat of the reaction Hence, the proportion of the volume of the catalyst based on the entire volume of the reactor is small, and because of the limit in making the tube sheets, the capacity of the apparatus in one train is remarkably restricted.

To use the reactor effectively, it would be possible to fill the catalyst into the shell side of the reactor. This method, however, will give rise to various problems. For example, in order to remove the heat of the reaction effectively, heat transfer tubes must be incorporated regularly and elaborately. The operation of replacing the catalyst is difficult This method also has difficulty in achieving uniform gas dispersion.

(3) The mixed alcohol used as a fuel preferably contains large amounts of higher alcohols such as ethanol, propanol and butanol in addition to methanol, and the amount of heat generated per unit weight of the product is much higher than in the case of methanol synthesis. In the synthesis of mixed alcohol, it is desirable to increase the amount of the mixed alcohol as much as possible and inhibit formation of hydrocarbons as by-products. Accordingly, the optimum temperature range for increasing the selectivity for alcohols is very narrow. For these reasons, the synthesis of mixed alcohol requires more efficient heat removal and more rigorous temperature control than the methanol synthesis.

The present inventors considered that methanol synthesis in a fluidized catalyst bed would be advantageous in solving the above problems associated with the construction of a large-sized apparatus for production of methanol or mixed alcohol. Based on this thought, the inventors have studied and developed a process in a reactor using a fluidized bed catalyst.

Consequently, the inventors have found that by synthesizing methanol under specific reaction conditions using a suitable fluidized bed catalyst, a good fluidized state of the catalyst can be obtained and the heat of the reaction can be efficiently removed; and that since the concentrations of effective components [i.e., carbon oxides ($CO+CO_2$)] in the reaction gas can be increased markedly, the efficiency of the reaction apparatus can be improved greatly.

Thus, according to the present invention, there is provided a process for producing methanol or mixed alcohol which comprises reacting a synthesis gas containing hydrogen and carbon monoxide and/or carbon dioxide in a fluidized catalyst bed, wherein (a) catalyst particles having an average particle diameter of not more than 150 microns and a particle density of at least 1.7 $g/cm^3$ are used as the fluidized catalyst, and (b) the catalyst particles are contacted with the synthesis gas at a superficial linear velocity of at least 0.2 m/sec. under a pressure of 40 to 200 atmospheres.

In the present specification and claims, the term "mixed alcohol" denotes a mixture of a major proportion of methanol with higher alcohols such as ethanol, propanol and butanol, which is mainly used as a fuel.

Figure 1:
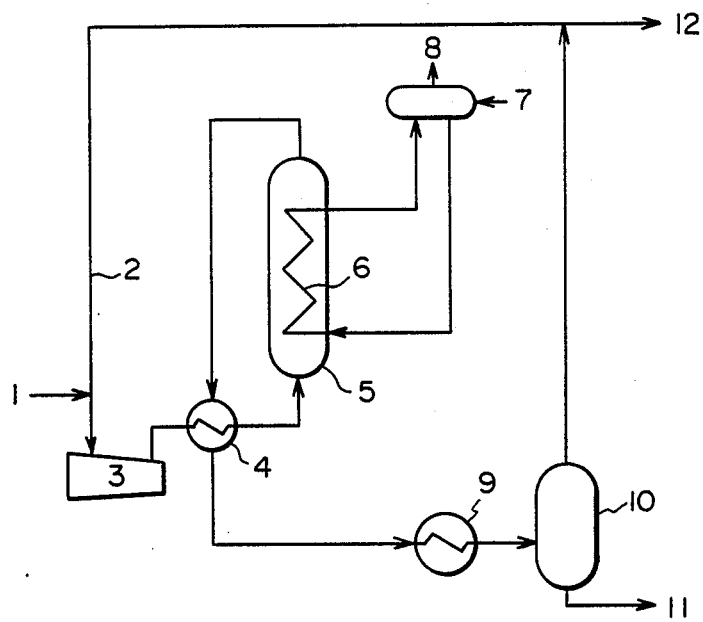
FIG. 1 is a flow chart of the process for the production of methanol or mixed alcohols according to an embodiment of the present invention.

Any fluidized bed catalyst normally used in the production of methanol or mixed alcohol from synthesis gas containing hydrogen and carbon monoxide and/or carbon dioxide may be used in the process of this invention. Such catalysts include, for example, those described in the above-cited Japanese Laid-Open Patent Publications Nos. 84142/1985 and 122040/1985 and U.S. Pat. No. 4,666,945. Examples of fluidized catalysts that can be preferably used in this invention are copper-zinc-zirconium(and/or aluminum) type catalysts for synthesis of methanol, and alkali added copper-zinc-zirconium (and/or aluminum) type catalysts for synthesis of mixed alcohol. These preferred catalysts can be prepared by known methods described in the above-cited patents. For example, the above catalysts can be produced by preparing a mixture composed of water-insoluble compounds of copper, zinc and (zirconium and/or aluminum) convertible respectively to oxides of copper, zinc and (zirconium and/or aluminum) oxides under calcination conditions, adding at least one alkali component where the catalyst is intended for production of mixed alcohol, drying the mixture, and calcining it.

In the production of the above catalyst, the starting uniform mixture composed of water-insoluble copper-, zinc-, and (zirconium- and/or aluminum) compounds can be prepared, for example, by various methods to be described below.

(a) A method which comprises adding a suitable precipitating agent to a mixed aqueous solution of water-soluble copper-, zinc-, and (zirconium- and/or aluminum) compounds to coprecipitate a mixture of water-insoluble copper-, zinc-, and (zirconium- and/or aluminum) compounds.

(b) A method wherein from a mixed aqueous solution of any two or three of a water-soluble copper compound, a water-soluble zinc compound, a water-soluble zirconium compound and a water-soluble aluminum compound, two or three water-insoluble compounds of the metals of the two or three soluble compounds are coprecipitated, the remaining water-soluble metal compound is added and dissolved in the coprecipitate-containing slurry and a water-insoluble compound of its metal is precipitated; or a slurry of water-insoluble compound of the metal of the remaining water-soluble metal compound separately precipitated is added to the above slurry containing the coprecipitate; or the above procedure is conducted in a reverse sequence.

(c) A method which comprises precipitating a water-insoluble copper compound, a water-insoluble zinc compound, and a water-insoluble zirconium compound and/or a water insoluble aluminum compound separately from an aqueous solution of a water-soluble copper compound, an aqueous solution of a water-soluble zinc compound, and an aqueous solution of a water-soluble zirconium compound and/or an aqueous solution of a water-soluble aluminum compound and mixing them in the form of a precipitate-containing slurry; or separating the precipitates by filtration and then kneading them with one another.

(d) A method wherein in order to form a mixed aqueous slurry of a water-insoluble copper and/or zirconium compound and/or aluminum compound and a water-insoluble zinc compound in the above method (b), zinc oxide or zinc hydroxide is added to a water-insoluble copper and/or zirconium compound and/or aluminum compound precipitated from an aqueous solution of a water-soluble copper and/or zirconium compound and/or aluminum compound to form an aqueous slurry and then carbon dioxide gas is blown into the aqueous slurry to convert zinc oxide or zinc hydroxide to basic zinc carbonate.

The alkali component may be added to the precipitation reaction system in any desired stage in each of the methods (a) to (d) described above.

Water-soluble copper compounds used as starting materials in these methods include water-soluble copper salts usually employed for the preparation of the aforesaid conventional catalysts Specific examples are cupric nitrate, cupric acetate and cupric oxalate. Those which do not contain elements acting as catalyst poisons such as halogen and sulfur are preferred. Cupric nitrate is especially preferred.

Water-soluble zinc compounds may be any water-soluble zinc salts which are usually employed for the preparation of the aforesaid conventional catalysts. Specific examples include zinc nitrate and zinc acetate. Of these salts, preferred are those not containing elements that become catalyst poisons such as halogen and sulfur. Zinc nitrate is particularly preferred.

Basic zinc carbonate obtained by blowing carbon dioxide gas into a suspension of zinc oxide or zinc hydroxide may likewise be used as the water-insoluble zinc compound.

Examples of the water-soluble zirconium compound that can be used in the above methods include organic or inorganic acid salts of zirconium such as zirconium oxynitrate and zirconium acetate. Preferably, these salts neither contain elements that become catalyst poisons, such as halogen and sulfur. Zirconium oxynitrate is especially preferred.

In order to form a water-insoluble zirconium compound, it is also possible to use zirconium compounds which are soluble in suitable solvents and can form a precipitate under suitable conditions, for example, zirconium alkoxides such as zirconium tetrabutoxide. The zirconium alkoxide can dissolve in a solvent such as an alcohol and upon addition of water, form a water-insoluble zirconium compound.

Examples of the water-soluble aluminum compound that can be used in the above methods include organic or inorganic acid salts of aluminum such as aluminum nitrate and aluminum acetate. Preferably, these salts neither contain elements that become catalyst poisons, such as halogen and sulfur. Aluminum nitrate is especially preferred.

In order to form a water-insoluble aluminum compound, it is also possible to use aluminum compounds which are soluble in suitable solvents and can form a precipitate under suitable conditions, for example, aluminum alkoxides such as aluminum isoproxide. The aluminum alkoxide can dissolve in a solvent such as an alcohol and upon addition of water, form a water-insoluble aluminum compound.

In the aforesaid methods, examples of the precipitating agent that can be used in the (co)precipitation of the water-insoluble copper and/or zinc and/or zirconium and/or aluminum compound(s) from the aqueous solution(s) of the water-soluble copper and/or zinc and/or zirconium and/or aluminum compound(s) may be water-soluble alkaline substances such as ammonia; alkali carbonates such as sodium carbonate, potassium carbonate, lithium carbonate and ammonium carbonate, alkali bicarbonates such as sodium bicarbonate, potassium bicarbonate and ammonium bicarbonate; and alkali metal hydroxides such as sodium hydroxide, potassium hydroxide and lithium hydroxide. The precipitating agent can usually be employed in an amount of at least 0.8 equivalent, preferably 1 to 2 equivalents, more preferably 1.0 to 1.3 equivalents, per equivalent of the water-soluble metal compound to be subjected to precipitation.

The reaction of forming the precipitate of the water-insoluble metal compound(s) from the aqueous solution(s) of the water-soluble metal compound(s) can be performed according to methods known per se, for example the methods described in U.S. Pat. Nos. 3,971,735 and 4,305,842 and UK Patent Application No. 2064352A. The reaction may be carried out, for example, at room temperature or if required, at an elevated temperature of up to about 90° C. Under these conditions, the reaction can proceed smoothly and be terminated almost quantitatively within several minutes to several tens of minutes.

The concentration of each of the water-soluble metal compounds in the aqueous solution in the precipitation reaction is not critical and can be varied broadly depending upon the types of the compounds. Generally, it is 0.05 mole/liter to the limit of dissolution of the compound(s), preferably 0.1 to 5 moles/liter.

The uniform mixture so formed of the water-insoluble copper, zinc and zirconium and/or aluminum compounds is filtered, washed if necessary and then formed into a slurry in a concentration suitable for pulverization. The slurry is molded into fine particles by, for example, spray-drying or dropping it onto an oil in a usual manner.

The concentration of the slurry varies with the composition of the uniform mixture, pulverizing method, etc. Generally, it is convenient to set the concentration such that the solids content is 5 to 40% by weight, preferably 10 to 30% by weight, based on the aqueous medium.

In preparing mixed alcohol, alkali component can be added to an aqueous solution containing the above mixture of copper, zinc, and (zirconium and/or aluminum) compounds at any desired stage during formation of the uniform mixture of water-insoluble copper, zinc, and (zirconium and/or aluminum) compounds.

Examples of the alkali component to be added are potassium carbonate, rubidium carbonate and cesium carbonate.

The water-insoluble copper, zinc, and (zirconium and/or aluminum) compounds which are formed as stated above can be converted substantially to copper, zinc, and (zirconium and/or aluminum) oxides under calcination conditions to be described. Specific examples of such compounds are basic copper carbonate, copper hydroxide, copper carbonate, basic zinc carbonate, zinc hydroxide, zinc carbonate, basic zirconium carbonate, zirconium hydroxide, zirconium carbonate, and aluminum hydroxide.

These water-insoluble copper, zinc, zirconium, aluminum and alkali components are included in the aforesaid mixture in amounts corresponding to the desired contents of copper oxide, zinc oxide, zirconium oxide and/or aluminum oxide and alkali component in the final catalyst product.

The catalyst precursor composition of the above mixture composed of water-insoluble copper, zinc, and zirconium and/or aluminum compounds and optionally containing at least one alkali component may have a solids content of 5 to 40% by weight, preferably 10 to 30% by weight, more preferably 20 to 30% by weight.

The catalyst precursor composition is then molded into fine particles and dried. The molding and drying may be performed as separate steps. Generally, however, it is convenient to perform them by using a particle-forming method in which molding into fine particles and drying of the fine particles can be carried out nearly simultaneously. Spray-drying and dropping into an oil may be cited as examples of such a particle-forming method. Spray-drying is especially preferred.

The catalyst precursor particles so prepared are then calcined. The calcination can be carried out by a method known per se. For example, the catalyst precursor particles are heated at a temperature of at least 280° C., preferably 300° to 500° C., for about 0.3 to 3 hours in an atmosphere of air, a combustion gas, etc. in a calcination furnace such as an electrical furnace or a gas calcination furnace.

Fluidized catalyst particles prepared as above and preferably used in the process of this invention may consist essentially of an intimate mixture of three or four essential components, copper oxide, zinc oxide, and zirconium oxide and/or aluminum oxide. The proportions of these three or four components in the catalyst may be as follow:

|  | General range (wt. %) | Preferred range (wt. %) | More preferred range (wt. %) |
| --- | --- | --- | --- |
| Copper oxide | 10–67 | 20–55 | 30–45 |
| Zinc oxide | 1.5–47 | 5–40 | 10–30 |
| Zirconium oxide and/or aluminum oxide | 30–70 | 40–60 | 45–55 |

The content of the alkali component which may be included in the catalyst as an optional component is generally up to 5% by weight, specifically 0.3 to 5% by weight, preferably 0.5 to 3% by weight. The ratio of copper oxide to zinc oxide in the catalyst composition is not strictly limited and can be changed depending upon the conditions under which a reaction of synthesizing methanol or mixed alcohols is carried out in the presence of the above catalyst. Usually, it is advantageous that copper oxide and zinc oxide are present in such proportions that the Cu/Zn atomic ratio is from 0.5/1 to 20.0/1, preferably from 0.8/1 to 15.0/1, more preferably from 0.8/1 to 5/1.

One characteristic feature of the process of this invention resides in the use of fluidized catalyst particles prepared as above which have an average particle diameter of not more than 150 microns. If the average diameter is larger than this limit, the fluidized condition of the catalyst layer is aggravated and the efficiency of contact between the catalyst and the reaction gas is reduced, and the reaction yield is drastically lowered. Accordingly, the fluidized catalyst used in this invention preferably has an average particle diameter of 30 to 150 microns, particularly 40 to 120 microns.

It is also critical that the fluidized catalyst particles used in the process of this invention have a particle density of at least 1.7 g/cm$^3$, preferably 2.0 to 3.3 g/cm$^3$. If the particle density is lower than 1.7 g/cm$^3$, the required volume of the catalyst increases and the amount of the catalyst which scatters with the reaction gas also increases. Hence, the catalyst collecting device (such as a cyclone) used must be increased in size. Furthermore, the catalyst layer swells to a greater extent, and at a relatively low superficial linear velocity, the catalyst layer reaches the top of the reactor. As a result, the catalyst collecting device becomes overloaded, and the reactor may possibly fail to work. For this reason, a large-sized reactor becomes necessary or the process is not economical.

The term "particle density", as used herein, denotes the density of the catalyst particles, and is calculated in accordance with the following equation.

$$\rho_p = \frac{1}{1/\rho_s + V_p} \ [g/cm^3]$$

The variables in the above equation have the following meanings.

$\rho_s$: the true density of the substance constituting the particles (g/cm$^3$)

$V_p$: the pore volume (cm$^3$/g)

$\rho_p$: the particle density (g/cm$^3$)

The catalyst particles prepared as above are subjected to an activation treatment such as reduction with hydrogen as is usually the case, and then used as a fluidized bed catalyst in the production of methanol or mixed alcohol by reacting synthesis gas containing hydrogen and carbon monoxide and/or carbon dioxide.

The activation treatment of the catalyst may be carried out in a customary manner, for example, by reducing it with a hydrogen-containing gas. For example, it is carried out in a reducing atmosphere such as a starting gas for synthesis of methanol or mixed alcohol by raising the temperature of the catalyst gradually from about 140° C. to avoid abrupt generation of heat, and finally maintaining the catalyst at 240° C. for 3 hours.

The synthesis gas used as a starting material in the process of this invention may be any conventional one used in the production of methanol or mixed gas. For example, it may be a gas containing hydrogen and carbon monoxide and/or carbon dioxide which results from steam reforming of natural gas or naphtha or from partial oxidation of petroleum products such as natural gas, coal, light oil and heavy oil. Typical compositions of such synthesis gases are tabulated below.

| Component | Synthesis gas (mole %) | | |
|---|---|---|---|
| | Steam reforming of natural gas | Steam reforming of naphtha | Partial oxidation of coal gas |
| CO | 15.6 | 16.0 | 27.2 |
| CO$_2$ | 7.3 | 12.2 | 4.0 |
| H$_2$ | 74.7 | 70.0 | 67.8 |
| CH$_4$ | 2.1 | 1.8 | — |
| N$_2$ | 0.3 | — | 1.0 |

Methanol or mixed alcohol from the synthesis gas in a fluidized catalyst bed may be carried out by known methods, for example the method described in U.S. Pat. No. 3,971,735. In the process of this invention, however, it is critical that the contacting of the synthesis gas with the fluidized catalyst bed should be carried out under a pressure of 40 to 200 atmospheres, preferably 50 to 150 atmospheres. If the contacting pressure is lower than 40 atmospheres, the reaction temperature should be lowered because of the equilibrium. Hence, the rate of the reaction tends to decrease. The results of experiments conducted by the present inventors show that under such lower pressures, slugging tends to take place and a good fluidized condition cannot be maintained. On the other hand, if the pressure is higher than 200 atmospheres, the compression power of the synthesis gas increases and the unit cost of the fuel required increases undesirably.

The rate of feeding the gas into the fluidized catalyst bed in the process of this invention, as the superficial linear velocity, is at least 0.2 m/sec, preferably 0.3 to 0.6 m/sec. If the superficial linear velocity is too low, the size of the reactor per unit weight of the product increases, and the coefficient of heat transmission decreases.

The reaction temperature is usually 180° to 500° C., preferably 200° to 400° C., more preferably 200° to 300° C. for production of methanol and 250° to 350° C. for production of mixed alcohol.

One embodiment of the production of methanol or mixed alcohol in accordance with this invention will be described more specifically with reference to a flow sheet attached as FIG. 1.

In FIG. 1, the starting synthesis gas 1 joins a circulating gas 2 from a separator 10, and elevated in pressure at a circulator 3. The mixture is pre-heated in a heat-exchanger 4 by the outlet gas of the reactor, and then enters a fluidized bed catalyst reactor 5. A heat transmission tube 6 is installed within the reactor to recover the heat of the reaction and heat the boiler feed water from a line 7 for example. Thus, steam having a pressure of 20 to 150 kg/cm$^2$, is recovered from a line 8. A cyclone or the like usually installed in the reactor separates the catalyst particles from the reaction gas. The outlet reaction gas preheats the inlet gas of the reactor at the heat-exchanger 4 and is cooled at a cooler 9. Condensed methanol or mixed alcohol and water are separated from the separator 10, and discharged from a line 11. These condensed liquids are, as required, purified in a distillation device to obtain methanol or mixed alcohol as a final product.

Part of the gas from the separator 10 is discharged out of the system via a line 12.

It is said that in a reaction effected by using a fluidized bed catalyst to which the process of this invention pertains, with an increase in the flow rate of the gas, the catalyst bed changes from a homogeneous phase fluidized bed to a bubbling fluidized bed, a turbulent bed, a fast fluidized bed and a dilute phase flow bed. By using the aforesaid specific conditions in the process of this invention, the reaction in this invention is carried out in a dense phase catalyst in an operating zone of the turbulent bed fluidized bed and an operating zone including part of the bubbling fluidized bed and the fast fluidized bed. Hence, under the conditions specified in this invention, a stable fluidized condition free from channeling or slugging can be obtained, and the reaction can be carried out effectively. Accordingly, the present invention can achieve the following advantages.

(1) The heat of the reaction can be effectively removed from the catalyst, and a gas having a high carbon oxide ($CO+CO_2$) content can be introduced into the reactor. This results in a marked increase in production rate per unit amount of the catalyst. In other words, the size of the reactor per unit production rate can be reduced as compared with the prior art, and the amount of the catalyst used can also be reduced.

(2) Since the concentration of carbon oxides in the inlet gas of the reactor can be increased, the concentration of methanol in the outlet gas of the reactor can be increased to, for example, about 15% in the synthesis of methanol. Accordingly, the amount of the circulating gas in the synthesis system can be greatly decreased, and the compression power of the circulating gas can be drastically decreased.

(3) Since in the process of this invention using the fluidized catalyst bed, the catalyst particles heated by the heat of the reaction move, the heat is also transmitted well from the catalyst particles to the reaction gas to thereby provide a nearly uniform temperature distribution. Moreover, the coefficient of heat transfer to heat transfer tubes is high so that the heat can be removed efficiently. Because of such thermal properties, it is easy to insert a heat transfer tube into the fluidized catalyst layer Since the coefficient of heat transfer is high and the required area of heat transfer is small, it is very easy to design and build the reactor.

(4) Since the catalyst is fluidized in the reactor and a nearly uniform temperature distribution can be obtained, the entire catalyst in the reactor can be effectively utilized For this reason, the operation can be continued for an extended period of time at a high STY, and the life of the catalyst is prolonged.

(5) Because of the increase of STY, the size of the reactor can be decreased. Since the amount of the circulating gas is decreased, the diameter of the pipes connected to the reactor can be decreased. Accordingly, the synthesis apparatus on the whole can be reduced in size and the construction cost can be decreased.

(6) Since the size of the reactor and the amount of the circulating gas can be reduced, the plant capacity of the methanol or mixed alcohol production in one train can be increased in size beyond the limit with conventional fixed bed catalyst reactors.

(7) Since the reaction heat is recovered in a high temperature level and the difference between the reaction temperature and the heat recovery temperature is small in the fluidized bed, a large quantity of the reaction heat is efficiently recovered. This enables "energy unit" to be reduced in connection with the reduction of gas circulating power.

As stated above, the process of this invention has various excellent industrial advantages and greatly contributes to the industrial production of methanol or mixed alcohol.

The following examples illustrate the present invention more specifically.

CATALYST PREPARATION EXAMPLE 1

Ammonium carbonate (400 g) was dissolved in 20 liters of deionized water, and the solution was heated to 50° C. A solution kept at 50° C. of 317.4 g of copper nitrate trihydrate and 294.5 g of zinc nitrate hexahydrate in 5 liters of deionized water was added to the solution with stirring to form a precipitate. The solution containing the precipitate was heated to 80° C. for 30 minutes, aged for 30 minutes, and then allowed to cool to 55° C. Then, 2 liters of a solution containing 109 g of 10% alumina sol was added, and the mixture was stirred for 10 minutes. Then, 5 liters of a solution kept at 40° C. of 377.8 g of zirconium oxynitrate dihydrate and 10 liters of a solution kept at 40° C. of a solution of 327.6 g of ammonium bicarbonate were added simultaneously with stirring, the mixture was stirred further for 30 minutes. The resulting insoluble precipitate was filtered and washed, and deionized water was added to adjust the solids concentration of the slurry to 25% by weight. The slurry was kneaded for 1 hour, and then dried by a spray dryer with heated air at a dryer inlet temperature of 250° C. to obtain spherical particles. The particles were calcined at 380° C. in an air current for 1.5 hours to give 230 g of a catalyst 1.

CATALYST PREPARATION EXAMPLE 2

Copper nitrate trihydrate (321.3 g), 297.5 g of zinc nitrate hexahydrate and 374.2 g of zirconium nitrate dihydrate were dissolved in 10 liters of deionized water and the solution was maintained at 60° C. The solution was poured into a solution kept at 60° C. of 631 g of ammonium bicarbonate in 30 liters of deionized water to form an insoluble precipitate. The solution containing the precipitate was stirred for 1 hour at 60° C., heated to 80° C. over the course of 30 minutes, and stirred further for 30 minutes The mixture was then allowed to cool, and was filtered. The filtrate was washed with 10 liters of deionized water four times. To the resulting cake was added an aqueous solution of 1.6 g of cesium carbonate in 10 ml of deionized water. Deionized water was further added to adjust the solids concentration of the slurry to 25% by weight. The slurry was kneaded for 1 hour, and dried by a spray dryer with heated air at a dryer inlet temperature of 250° C. to obtain spherical particles. The particles were calcined at 380° C. for 1.5 hours in an air current to give 350 g of a catalyst 2.

This catalyst contains an alkali component and is used for production of mixed alcohol.

CATALYST PREPARATION EXAMPLE 3

A catalyst 3 having a large average particle diameter was prepared as in Catalyst Preparation Example 1 except that the drying of the slurry was carried out by using a spray nozzle of a large diameter.

CATALYST PREPARATION EXAMPLE 4

A catalyst 4 having a low particle density was obtained as in Catalyst Preparation Example 1 except that the solid concentration of the slurry was adjusted to 15% by weight.

The properties of the catalysts obtained in Catalyst Examples 1 to 4 are shown in Table 1 below.

TABLE 1

| Preparation Example No. | 1 | 2 | 3 | 4 |
|---|---|---|---|---|
| Catalyst composition (atomic ratio) | | | | |
| Cu | 1.33 | 1.33 | 1.33 | 1.33 |
| Zn | 1.0 | 1.0 | 1.0 | 1.0 |
| Zr | 1.43 | 1.40 | 1.43 | 1.43 |
| Al | 0.11 | — | 0.11 | 0.11 |
| Cs | — | 0.01 | — | — |
| Average particle diameter (microns) | 48 | 53 | 170 | 49 |
| Particle density (g/cm$^3$) | 2.61 | 2.86 | 2.65 | 1.4 |

EXAMPLE 1

In the flowchart shown in FIG. 1, a fluidized bed catalyst reactor having an inside diameter of 320 mm and a height of 30 m was installed. Catalyst 1 was charged into this reactor and fluidized with nitrogen gas. Hydrogen gas was gradually added at 180° C. to reduce the catalyst.

After the reduction of the catalyst, a starting synthesis gas composed of 21.38 mole % of CO, 8.25 mole % of CO$_2$, 67.53 mole % of H$_2$, 2.00 mole % of CH$_4$, 0.59 mole % of N$_2$ and 0.15 mole % of H$_2$O was introduced into the reactor, and reacted.

The reaction conditions were as follows:

Pressure of the gases fed into the reactor:

102.5 kg/cm$^2$

Space velocity (SV): 9480 l/hour
Ratio of the circulating gas/synthesis gas: 1.5

At an average temperature of 270° C. in the dense phase catalyst bed, the concentration of methanol was 14.1 mole %. The amount of methanol produced was 20 tons a day.

In the fluidized bed catalyst reactor, the reaction proceeded very well and a high methanol concentration was obtained.

Since it is presumed that about twice as large an amount of the catalyst and about 4 times as large an amount of the circulating gas are required in a conventional fixed bed quenching-type reactor in order to obtain the same amount of methanol at the same pressure and temperature. Hence, the process of this invention using a fluidized bed catalyst reactor is a very advantageous method.

EXAMPLE 2

Catalyst 2 was charged into the same reactor as used in Example 1, and reduced by the same method as in Example 1. Then, a starting synthesis gas composed of 31.77 mole % of CO, 0.78 mole % of CO$_2$, 65.35 mole % of H$_2$, 1.37 mole % of CH$_4$ and 0.73 mole % of N$_2$ was introduced into the reactor, and reacted.

The reaction conditions were as follows:
Pressure of the gases fed into the reactor:

70 kg/cm$^2$

Space velocity (SV): 8700 l/hour
Ratio of the circulating gas/synthesis gas 2.6

At an average temperature of 340° C. in the dense phase catalyst bed, the STY of mixed alcohol was 770 kg/m$^3$.hr. The products in the outlet gas of the reactor were 6.95 mole % of alcohols, 0.16 mole % of hydrocarbons and 0.63 mole % of CO$_2$. In the present example, the amounts of by-products such as hydrocarbons and CO$_2$ were very small, and a high alcohol selectivity was obtained together with a high STY.

EXAMPLE 3

Using a fluidized bed catalyst reactor having an inside diameter of 73.9 mm and a height of 5 m and fitted with a temperature controlling jacket, catalysts 1, 3 and 4 shown in Table 1 were used at different space velocities.

In each run, 5 liters of the catalyst was charged, and reduced as in Example 1.

After the reduction of the catalyst, a synthesis gas composed of 10.6 mole % of CO, 9.72 mole % of CO$_2$, 65.33 mole % of H$_2$, 10.24 mole % of CH$_4$, 3.78 mole % of N$_2$ and 0.07 mole % of H$_2$O was introduced into the catalyst bed. The reaction conditions were adjusted so that under an inlet gas pressure of 80 kg/cm$^2$ in the reactor, the average temperature of the dense phase catalyst bed became 260° C.

Figure 2:
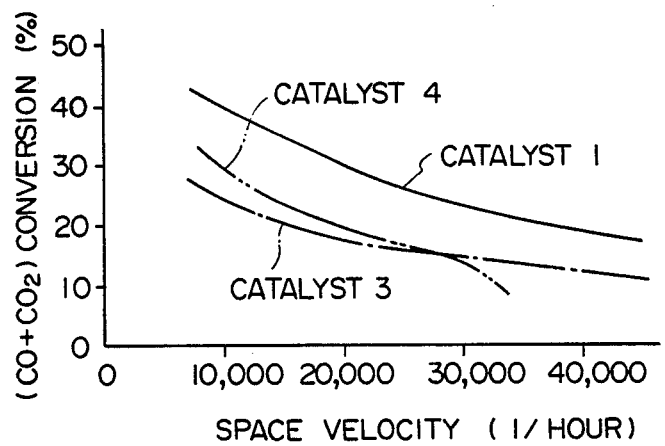
FIG. 2 is a graph of the conversion of carbon oxides by catalysts at different space velocities.

The reaction was carried out at different space velocities, and the conversion of carbon oxides (CO+CO$_2$) [to be referred to simply as the conversion] obtained are shown in Table 2 and FIG. 2.

TABLE 2

| Space velocity (l/hr) | Conversion of carbon oxides (%) | | |
|---|---|---|---|
| | Catalyst 1 | Catalyst 3 | Catalyst 4 |
| 8,800 | 41.6 | 25.6 | 32.0 |
| 17,600 | 32.0 | 18.0 | 21.4 |
| 26,400 | 25.6 | 16.2 | 16.4 |
| (30,800) | | | (13.7) |
| 35,200 | 21.4 | 13.5 | — |
| 43,900 | 17.3 | 11.1 | — |

With catalyst 1, the conversion at a space velocity of 8,800 l/hr was 41.6 % and the conversion at a space velocity of 43,900 l/h was 17.3%, whereas with catalyst 3 having a larger particle diameter, the conversion at a space velocity of 8,800 l/hr was 25.6% showing a decrease of about 40%. The space velocity of 8,800 l/hr corresponds to a superficial linear velocity, based on the inlet of the reactor, of 9.7 cm/sec. With catalyst 3, slugging was observed, and evidently, the state of contact between the reaction gas and the catalyst was aggravated. This state did not change even when the amount of the gas introduced and the space velocity were increased. It is presumably because the particle diameter of the catalyst was too large.

The catalyst 4 had a low particle density, and the amount of its effective active components was about 55% of the catalyst 1. The conversion decreased at a low space velocity because the amount of the effective active components was small. At a space velocity of more than 26,400 l/hr (superficial linear velocity based on the inlet of the reactor 29 cm/sec), the operating condition abruptly became poor, and finally the operation failed. This was because the dense phase catalyst layer reached near the top of the tower as a result of the increased bed expansion ratio, and overpowered the capacity of the particle collecting system.

What is claimed is:

1. A process for producing methanol or a mixture of methanol and higher alcohols from a synthesis gas containing hydrogen and carbon monoxide and/or carbon dioxide, which comprises:

(a) passing the synthesis gas through a fluidized bed catalytic reactor at a superficial linear velocity of at least 0.2 m/sec., a temperature of 180° to 500° C. and a pressure of 50 to 150 atmospheres, said fluidized bed catalytic reactor containing a catalyst for use in the production of methanol or a mixture of methanol and higher alcohols, said catalyst comprising particles having an average particle diameter of 30 to 150 μm and a particle density of 1.7 to 3.3 g/cm$^3$, whereby methanol or a mixture of methanol and higher alcohols is produced in an exothermic reaction, and simultaneously with the reaction recovering heat from the reaction by passing a heat transfer medium through a heat transmission tube in said reactor, (b) cooling the gas stream resulting from the reaction containing methanol or mixture of methanol and higher alcohols, thereby condensing the methanol or mixture of methanol and higher alcohols into a liquid, and (c) separating the liquid methanol or mixture of methanol and higher alcohols from the gas stream.

2. A continuous process for producing methanol or a mixture of methanol and higher alcohols from a synthetic gas containing hydrogen and carbon monoxide and/or carbon dioxide, which comprises:

(a) passing the synthesis gas through a fluidized bed catalytic reactor at a superficial linear velocity of at least 0.2 m/sec., a temperature of 180° to 500° C. and a pressure of 50 to 150 atmospheres, said fluidized bed catalytic reactor containing a catalyst for use in the production of methanol or a mixture of methanol and higher alcohols, said catalyst comprising particles having an average particle diameter of 30 to 150 μm and a particle density of 1.7 to 3.3 g/cm$^3$, whereby methanol or a mixture of methanol and higher alcohols is produced in an exothermic reaction, and simultaneously with the reaction recovering heat from the reaction by passing a heat transfer medium through a heat transmission tube in said reactor, (b) cooling the gas stream resulting from the reaction containing methanol or the mixture of methanol and higher alcohols, thereby condensing the methanol or mixture of methanol and higher alcohols into a liquid, (c) separating the liquid methanol or mixture of methanol and higher alcohols from the gas stream, (d) recycling the resultant gas for reuse, (e) mixing the recycled gas with new synthesis gas for passage through the fluidized bed catalytic reactor, and (f) repeating steps (a) through (e).

3. The process of claim 2 wherein the catalyst particles are contacted with the synthesis gas at a superficial linear velocity of 0.3 to 0.6 m/sec.

4. The process of claim 2 wherein the catalyst particles consist essentially of an intimate mixture of copper oxide, zinc oxide, and zirconium oxide and/or aluminum oxide.

5. The process of claim 2 wherein the catalyst particles consist essentially of an intimate mixture of copper oxide, zinc oxide, and zirconium oxide and/or aluminum oxide, and additionally at least one alkali component.

6. The process of claim 2, wherein the ratio of the recycled gas to the new synthesis gas is 1.5 to 2.6.

* * * * *